(12) United States Patent
Yonetani et al.

(10) Patent No.: US 11,099,073 B2
(45) Date of Patent: Aug. 24, 2021

(54) IDENTIFICATION APPARATUS, IDENTIFICATION SYSTEM, AND RESIN-SELECTING SYSTEM

(71) Applicant: CANON KABUSHIKI KAISHA, Tokyo (JP)

(72) Inventors: Yuki Yonetani, Kawasaki (JP); Shigeru Ichihara, Tokyo (JP); Yasuhiro Sekine, Yokohama (JP); Akira Yamamoto, Ageo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/892,017

(22) Filed: Jun. 3, 2020

(65) Prior Publication Data

US 2020/0292389 A1  Sep. 17, 2020

Related U.S. Application Data

(63) Continuation of application No. PCT/JP2018/043794, filed on Nov. 28, 2018.

(30) Foreign Application Priority Data

Dec. 5, 2017  (JP) .............................. JP2017-233788

(51) Int. Cl.
*G01J 3/44* (2006.01)
*G01J 3/02* (2006.01)
*G01N 21/65* (2006.01)

(52) U.S. Cl.
CPC ........... *G01J 3/4412* (2013.01); *G01J 3/0218* (2013.01); *G01N 21/65* (2013.01)

(58) Field of Classification Search
CPC ... G01J 3/44; G01J 3/02; G01N 21/65; G01N 21/658; G01N 2021/656

(Continued)

(56) References Cited

U.S. PATENT DOCUMENTS

2013/0229510 A1  9/2013 Killmann
2015/0377701 A1* 12/2015 Pawluczyk ........... G01J 3/0243
                                                356/301
2016/0000330 A1*  1/2016 Huang .................. G01J 3/0272
                                                600/476

FOREIGN PATENT DOCUMENTS

JP  H10-038807 A  2/1998
JP  2008-209128 A  9/2008
(Continued)

OTHER PUBLICATIONS

Yuta Yamaji et al.; "A Novel Separation Method for Plastic of Discarded Appliance Including Black Plastic by Using Raman Spectroscopy", Resources Processing, Feb. 2013, vol. 60, No. 2, pp. 65-71, doi: 10.4144/rpsj.60.65.

*Primary Examiner* — Md M Rahman
(74) *Attorney, Agent, or Firm* — Canon U.S.A., Inc. IP Division

(57) ABSTRACT

An identification apparatus identifies the kind of an object to be conveyed by a conveyor and includes an illumination optical system illuminating the object with light from a light source, a light capturing optical system capturing Raman-scattered light from the object, a spectral element dispersing the Raman-scattered light, a light-receiving element receiving the Raman-scattered light dispersed by the spectral element, and a data-processing unit acquiring spectral data of the Raman-scattered light from the light-receiving element and performs an identification process. An optical axis of the illumination optical system and an optical axis of the light capturing optical system intersect each other. The illumination optical system is an imaging optical system that has a numerical aperture for the conveyance surface smaller than that of the light capturing optical system for the conveyance surface, or a collimator optical system that converts the light from the light source into parallel light.

28 Claims, 5 Drawing Sheets

(58) Field of Classification Search
USPC .......................................................... 356/301
See application file for complete search history.

(56) References Cited

FOREIGN PATENT DOCUMENTS

| | | |
|---|---|---|
| JP | 2009-092458 A | 4/2009 |
| JP | 2010-133842 A | 6/2010 |
| JP | 2011-089085 A | 5/2011 |
| JP | 2011-226821 A | 11/2011 |
| JP | 2013-036971 A | 2/2013 |
| JP | 2014-113792 A | 6/2014 |
| JP | 2014-115193 A | 6/2014 |
| NO | 2012/035785 A1 | 3/2012 |
| NO | 2012/120779 A1 | 9/2012 |

\* cited by examiner

IDENTIFICATION APPARATUS, IDENTIFICATION SYSTEM, AND RESIN-SELECTING SYSTEM

CROSS-REFERENCE TO RELATED APPLICATIONS

This application is a Continuation of International Patent Application No. PCT/JP2018/043794, filed Nov. 28, 2018, which claims the benefit of Japanese Patent Application No. 2017-233788, filed Dec. 5, 2017, both of which are hereby incorporated by reference herein in their entirety.

BACKGROUND OF THE INVENTION

Field of the Invention

The present invention relates to an identification apparatus, an identification system that uses the identification apparatus, and a resin-selecting system.

Description of the Related Art

When resins such as various kinds of plastic or elastomer contained in household garbage or industrial waste are reused as the materials of new products, it is necessary to select the resins in the waste for every quality of material. In recycling facilities, waste is mechanically crushed into crushed substances containing, for example, an object or a metal piece, and the substances are separated in various ways.

In a method of separating objects such as plastic, Raman scattering is used. The use of the Raman scattering enables the quality of a resin material to be identified and enables an ingredient composition and the distribution thereof to be investigated. An identification system can have high throughput in a manner in which resin is conveyed by a conveyor such as a belt conveyor, and Raman-scattered light from the conveyed resin is detected for identification.

In Japanese Patent Application Laid-Open No. 2008-209128 and Japanese Patent Application Laid-Open No. H10-038807, an identification apparatus that identifies the kind of plastic by using Raman scattering is disclosed. In the identification apparatus disclosed in Japanese Patent Application Laid-Open No. 2008-209128, an illumination optical system that irradiates an object with a laser beam and a light capturing optical system that condenses Raman-scattered light from the object are coaxial with each other and perpendicular to a conveyance surface. A determination apparatus disclosed in Japanese Patent Application Laid-Open No. H10-038807 includes a laser device that is disposed such that a laser beam is diagonally incident on a conveyance surface and a Raman spectroscope that is disposed perpendicularly to the conveyance surface.

Objects to be identified have nonuniform shapes and take various postures while being conveyed by a conveyor such as a belt conveyor. While each object is conveyed by the conveyor, the position thereof is likely to vary due to, for example, a vibration. Accordingly, while the object is conveyed by the conveyor, the position thereof in a height direction greatly varies, and the distance between the identification apparatus and the object to be identified greatly varies.

The Raman-scattered light is typically weak. Accordingly, to increase the intensity of the Raman-scattered light to be detected, it is necessary to irradiate the object with high-intensity light to increase the intensity of the Raman-scattered light to be generated and to capture the generated Raman-scattered light by using a highly efficient light capturing optical system. In the apparatus disclosed in Japanese Patent Application Laid-Open No. 2008-209128 in which the illumination optical system and the light capturing optical system are coaxial with each other, a great variation in the distance between the identification apparatus and the object results in a decrease in the intensity of the generated Raman-scattered light and a decrease in the intensity of the captured Raman-scattered light, and sensitivity is likely to decrease. In Japanese Patent Application Laid-Open No. H10-038807, none of optical settings for illumination and capturing is disclosed, and the influence of the variation in the distance between the identification apparatus and the object is not considered.

That is, each of the existing identification apparatuses that uses the Raman scattering has a problem in that a great variation in the distance between the identification apparatus and the object results in a great variation in the intensity of the Raman-scattered light, and this makes it difficult to make identification stably.

SUMMARY OF THE INVENTION

In view of the above problem, it is an object of the present invention to provide an identification apparatus that has a high degree of robustness against a variation in the distance between an identification apparatus and an object.

An identification apparatus according to an aspect of the present invention is an identification apparatus that identifies a kind of resin that is contained in an object to be conveyed by a conveyor. The identification apparatus includes an illumination optical system that illuminates the object on a conveyance surface of the conveyor with light from a light source, a light capturing optical system that captures Raman-scattered light from the object that is illuminated by the illumination optical system, a spectral element that disperses the Raman-scattered light that is captured by the light capturing optical system, a light-receiving element that receives the Raman-scattered light that is dispersed by the spectral element, and a data-processing unit that acquires spectral data of the Raman-scattered light from the light-receiving element and that performs a process of identifying the object, based on the spectral data. An optical axis of the illumination optical system and an optical axis of the light capturing optical system intersect each other. The illumination optical system is an imaging optical system that has a numerical aperture for the conveyance surface smaller than a numerical aperture of the light capturing optical system for the conveyance surface.

An identification apparatus according to another aspect of the present invention is an identification apparatus that identifies a kind of resin that is contained in an object to be conveyed by a conveyor. The identification apparatus includes capturing units each of which includes an illumination optical system that illuminates the object on a conveyance surface of the conveyor with light from a light source, and a light capturing optical system that captures Raman-scattered light from the object that is illuminated by the illumination optical system, the capturing units facing the conveyance surface of the conveyor and being arranged at different positions in a traverse direction of conveyance intersecting a conveyance direction of the conveyor, an optical fiber bundle that includes optical fibers that guide the Raman-scattered light that is captured by the capturing units, the optical fibers being bundled near an exit end of the optical fiber bundle, a spectral element that disperses a collection of the Raman-scattered light that is guided by the optical fiber bundle, a light-receiving element that receives the collection of the Raman-scattered light that is dispersed by the spectral element, and a data-processing unit that acquires spectral data of the collection of the Raman-scattered light from the light-receiving element and that performs an identification process. In each of the capturing units, an optical axis of the illumination optical system and an optical axis of the light capturing optical system intersect each other.

An identification apparatus according to another aspect of the present invention is an identification apparatus that identifies a kind of resin that is contained in an object to be conveyed by a conveyor. The identification apparatus includes an illumination optical system that illuminates the object on a conveyance surface of the conveyor with light from a light source, a light capturing optical system that captures Raman-scattered light from the object that is illuminated by the illumination optical system, a spectral element that disperses the Raman-scattered light that is captured by the light capturing optical system, a light-receiving element that receives the Raman-scattered light that is dispersed by the spectral element, and a data-processing unit that acquires spectral data of the Raman-scattered light from the light-receiving element and that performs a process of identifying the object, based on the spectral data. An optical axis of the illumination optical system and an optical axis of the light capturing optical system intersect each other. The illumination optical system is an imaging optical system that has an objective numerical aperture smaller than an objective numerical aperture of the light capturing optical system.

Further features of the present invention will become apparent from the following description of exemplary embodiments with reference to the attached drawings.

DESCRIPTION OF THE EMBODIMENTS

Embodiments for carrying out the present invention will hereinafter be described with reference to the drawings. The present invention is not limited to the embodiments described below. The present invention includes modifications and alterations that are appropriately made to the embodiments described below, based on the normal knowledge of the person skilled in the art without departing from the spirit of the present invention.

First Embodiment

Figure 1:
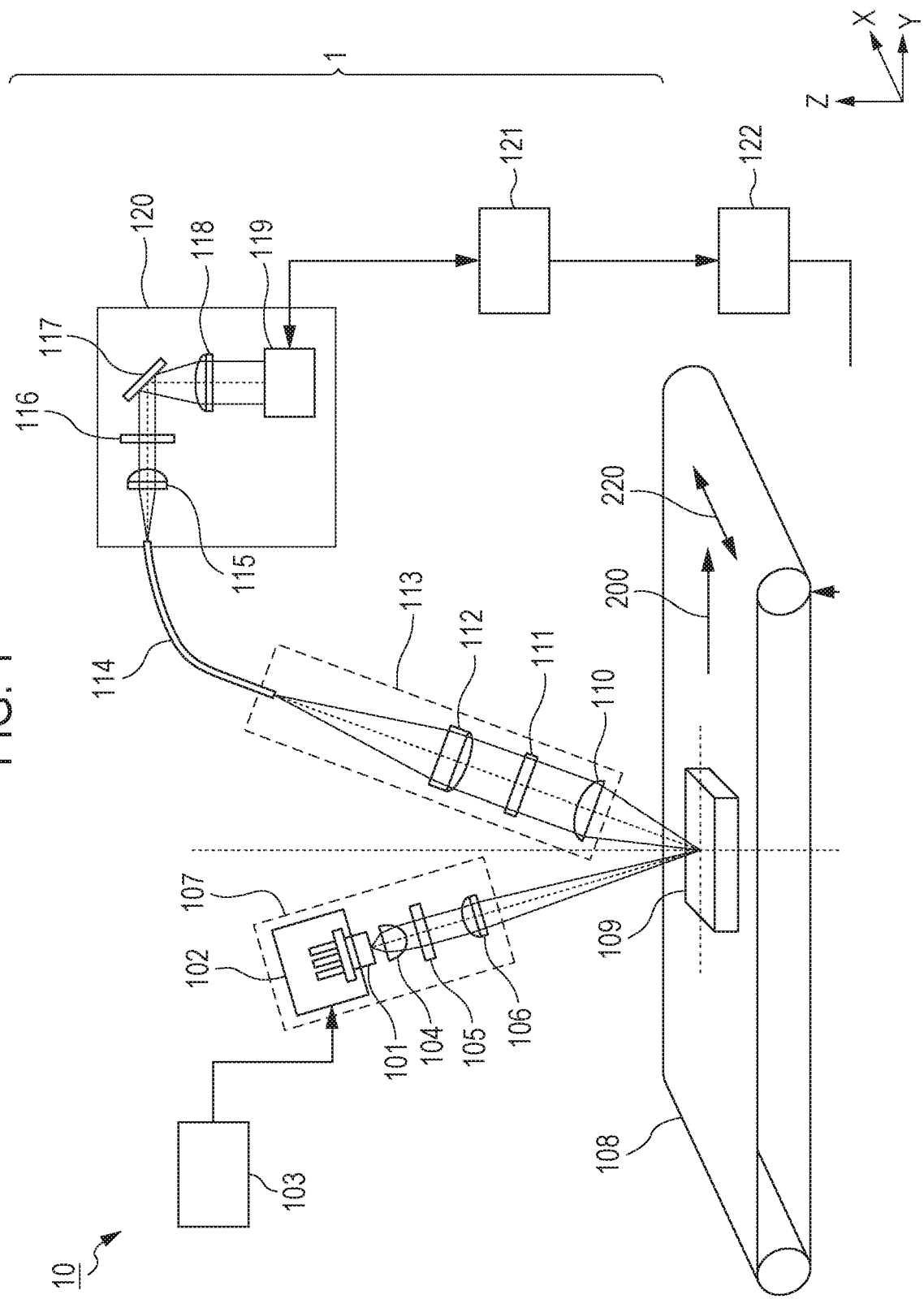
FIG. 1 schematically illustrates the structure of an identification system and an identification apparatus according to a first embodiment.

An identification apparatus according to a first embodiment of the present invention will be described with reference to FIG. 1. FIG. 1 schematically illustrates the structure of an identification system and the identification apparatus according to the first embodiment.

An identification apparatus 1 according to the present embodiment faces a conveyance surface of a conveyor 108 and identifies the kind of an object 109 that is conveyed by the conveyor 108. As illustrated in FIG. 1, the identification apparatus 1 includes an illumination optical system 107, a light capturing optical system 113, a spectral element 117, a light-receiving element 119, and a data-processing unit 121. An identification system 10 according to a modification to the present embodiment includes the conveyor 108, a conveyor-driving device 122, and the identification apparatus 1 that faces the conveyor 108. In FIG. 1, lines and directional straight lines that connect components represent optical paths and electric wiring.

The illumination optical system 107 illuminates the object 109 on the conveyance surface of the conveyor 108 with light from a light source. The object 109 that is illuminated by the illumination optical system 107 emits Raman-scattered light. The illumination optical system 107 includes a semiconductor laser 101, a laser mount 102, a laser driver 103, a collimator lens 104, a cylindrical lens 105, and a condensing lens 106.

The semiconductor laser 101 is the light source for the light with which the object 109 is illuminated. According to the present embodiment, the semiconductor laser 101 is a continuous-wave laser and radiates high-intensity light to generate the Raman-scattered light from the object 109. Regarding Raman scattering, the shorter the wavelength of illumination light, the higher the efficiency with which the Raman-scattered light is generated. The longer the wavelength of the illumination light, the smaller the amount of fluorescence that forms a background. An example of the light from the light source such as the semiconductor laser 101 can be light having a wavelength of 532 nm, 633 nm, or 780 nm. In the description herein, the light source of the illumination optical system 107 is the semiconductor laser 101 but is not limited thereto. Another laser light source such as a diode-pumped solid-state laser or a gas laser can be used.

The laser mount 102 holds the semiconductor laser 101 and dissipates heat. The laser driver 103 supplies an electric current to the semiconductor laser 101 via the laser mount 102, causes the semiconductor laser 101 to oscillate, and keeps the temperature of the semiconductor laser 101 constant at the same time.

The collimator lens 104 and the cylindrical lens 105 reduce the distribution of the light that is radiated from the semiconductor laser 101 and forms the light into parallel light. The cylindrical lens 105 may be another collimation optical element such as an anamorphic prism pair. The illumination optical system 107 may include a wavelength filter such as a laser line filter at a position on the pupil surface thereof. This improves wavelength characteristics of the light with which the object 109 is irradiated by the illumination optical system 107. The condensing lens 106 condenses the light from the semiconductor laser 101 on the object 109. The collimator lens 104, the cylindrical lens 105, and the condensing lens 106 are preferably composed of synthetic quartz in order to reduce fluorescence that forms a background and Raman-scattered light because the semiconductor laser 101 radiates the high-intensity light.

In the case of a semiconductor laser, an exit end typically has an oblong, elliptic shape. In this case, a section of parallel light that is collimated by a collimator optical system and a spot that is condensed by an imaging optical system also have an elliptic shape. In this case, the direction of the illumination optical system 107 is determined such that the major axis of an ellipse substantially coincides with a conveyance direction 200 of the conveyor 108, and this enables irradiation time of the light with which the object 109 is irradiated during conveyance to be increased. Consequently, the number of Raman-scattered light signals can be increased. That is, in the case where the spot of the light that is radiated by the illumination optical system 107 has an elliptic shape, an angle that is formed between the direction of the major axis of the spot of the light and the conveyance direction 200 of the conveyor 108 is preferably decreased. Specifically, the angle that is formed between the two directions is preferably no less than 0 degrees and no more than 15 degrees, more preferably no less than 0 degrees and no more than 5 degrees. With some structures of the illumination optical system 107, for example, in the case where the condensing lens 106 is not used, the direction of the major axis of an illumination region does not coincide with the conveyance direction 200. In this case, the direction in which the semiconductor laser 101 or the laser mount 102 is secured is changed such that the direction of the major axis of the illumination region coincides with the conveyance direction 200, or the entire illumination optical system 107 may be rotated about the optical axis when disposed.

The optical axis of the illumination optical system 107 is preferably inclined toward an upstream side or a downstream side in the conveyance direction 200 with respect to the normal to the conveyance surface of the conveyor 108 when disposed. This enables the spot of the light that is radiated by the illumination optical system 107 on the conveyance surface to be enlarged in the conveyance direction 200 of the conveyor 108. Consequently, the irradiation time of the light with which the object 109 is illuminated during conveyance can be increased, and the number of the Raman-scattered light signals can be increased.

The illumination optical system 107 thus defines the illumination region on the conveyance surface of the conveyor 108, and the illumination region is illuminated with the radiated light. Regarding the shape of the illumination region, the width in the conveyance direction 200 of the conveyor 108 is preferably greater than the width in a traverse direction 220 of conveyance intersecting the conveyance direction 200.

A plane containing the optical axis of the illumination optical system 107 and the optical axis of the light capturing optical system 113 is preferably substantially parallel to the conveyance direction 200 of the conveyor 108. Specifically, an angle that is formed between the plane and the conveyance direction 200 is preferably no less than 0 degrees and no more than 15 degrees, more preferably no less than 0 degrees and no more than 5 degrees, particularly preferably 0 degrees. That is, the plane and the conveyance direction 200 are particularly preferably parallel to each other. This enables the spot of the light that is radiated by the illumination optical system 107 on the conveyance surface to be enlarged in the conveyance direction 200 of the conveyor 108. Consequently, the irradiation time of the light with which the object 109 is illuminated during conveyance can be increased, and the number of the Raman-scattered light signals can be increased.

The conveyor 108 conveys the object 109 that is introduced from an object-supplying unit, not illustrated, to a measurement position at a constant speed. Any unit that can convey the object 109 placed on the conveyance surface can be used as the conveyor 108. For example, a belt conveyor can be used. The identification apparatus 1 according to the present embodiment measures Raman scattering while the object 109 is conveyed by the conveyor 108. After the measurement, the object 109 is continuously conveyed in the same direction and appropriately discharged into, for example, a basket for carry-out or a basket for selection (not illustrated).

The object 109 is a resin piece that is obtained by crushing, for example, household garbage or industrial waste. The resin in the present specification generally means a polymer, examples of which include a thermoplastic resin (plastic), a thermosetting resin, rubber, and an elastomer. The object 109 may contain various additives such as a glass or fiber filler or a flame retardant in addition to the resin. The identification apparatus 1 according to the present embodiment can identify the kind of the resin in the object, that is, the kind of the material of the object and can identify the presence or absence of the additives and the kind thereof.

The light capturing optical system 113 captures the Raman-scattered light from the object 109 that is illuminated by the illumination optical system 107. The Raman-scattered light that is captured by the light capturing optical system 113 is guided by a guide unit such as an optical fiber 114 to the spectral element 117. The light capturing optical system 113 includes an objective lens 110, an excitation light cutoff filter 111, and a fiber condensing lens 112.

The identification apparatus 1 may include the guide unit that guides the Raman-scattered light that is captured by the light capturing optical system 113 to the spectral element 117. Specifically, the identification apparatus 1 may include the optical fiber 114.

The objective lens 110 gathers the Raman-scattered light from the object 109 that is illuminated by the illumination optical system 107. The lens of the light capturing optical system 113, such as the objective lens 110, is preferably composed of synthetic quartz in order to reduce fluorescence that forms a background and Raman-scattered light because high-intensity light is radiated depending on the object 109 in some cases. In addition, the use of a cemented lens is preferably avoided to reduce a background from balsam and to inhibit the balsam from being separated due to generated heat. That is, the lens of the light capturing optical system 113, such as the objective lens 110, is preferably a single lens. The objective lens 110 is preferably an aspherical lens to improve the efficiency of coupling with the optical fiber 114 that serves as the guide unit.

The excitation light cutoff filter 111 is a wavelength filter such as a band-pass filter or a long-pass filter, shields light having at least a wavelength range in the light that is gathered by the objective lens 110, and allows the Raman-scattered light to pass therethrough. Consequently, unnecessary light for measurement of the Raman-scattered light is shielded, and the Raman-scattered light passes. In the perspective of filter characteristics, the excitation light cutoff filter 111 is preferably disposed in a parallel light bundle between the objective lens 110 and the fiber condensing lens 112, that is, on the pupil surface of the light capturing optical system 113.

The fiber condensing lens 112 couples the Raman-scattered light with the optical fiber 114. In the case where the excitation light cutoff filter 111 is inserted, the Raman-scattered light from the fiber condensing lens 112 can be ignored. Accordingly, priority is placed on the efficiency of coupling with the optical fiber 114, and an aberration is preferably reduced by using a cemented lens such as a doublet lens.

The optical fiber 114 guides the Raman-scattered light that is captured by the light capturing optical system 113 to a spectroscope 120. According to the present embodiment, the guide unit is the optical fiber 114 but is not limited thereto. Another guide unit such as an optical waveguide or a mirror may be used.

The spectroscope 120 includes at least a spectral element that disperses the Raman-scattered light that is captured by the light capturing optical system 113 and a light-receiving element that receives the Raman-scattered light that is dispersed by the spectral element, and disperses the Raman-scattered light to generate a spectrum signal. The spectroscope 120 includes an imaging lens 115, a long-pass filter 116, a diffraction grating 117 that serves as the spectral element, an imaging lens 118, and a CCD 119 that serves as the light-receiving element.

The imaging lens 115 converts the light from the optical fiber 114 into parallel light. The long-pass filter 116 is disposed between the imaging lens 115 and the diffraction grating 117, removes a remaining excitation light component, and allows only the Raman-scattered light to pass therethrough.

The diffraction grating 117 disperses the Raman-scattered light that is captured by the light capturing optical system 113 and causes the Raman-scattered light to one-dimensionally scatter at every wavelength. The imaging lens 118 images the light that is dispersed by the diffraction grating 117 on the CCD 119. The optical arrangement of components in the spectroscope 120 and a dispersing method may be appropriately changed into another arrangement and another method that are typically used such as Rowland arrangement and a Czerny-Turner method.

The CCD 119 is the light-receiving element that receives the Raman-scattered light one-dimensionally dispersed by the diffraction grating 117 serving as the spectral element and that converts the Raman-scattered light into an electrical signal. A spectrum signal that is generated by the CCD 119 is transmitted to a computer 121 that serves as the data-processing device. Here, the light-receiving element is an area image sensor that includes photoelectric converters such as photodiodes that are two-dimensionally arranged but is not limited thereto, provided that the light-receiving element can receive the Raman-scattered light that is dispersed by the spectral element at every wavelength component and can output a signal that represents the intensity thereof. Accordingly, the light-receiving element may be a line sensor that includes photoelectric converters that are one-dimensionally arranged. The light-receiving element can be a CMOS sensor.

The conveyor-driving device 122 drives the conveyor 108.

The computer 121 acquires the spectral data of the Raman-scattered light from the CCD 119 that serves as the light-receiving element. The computer 121 appropriately transmits a driving signal and a stop signal to the conveyor 108. The computer 121 extracts the Raman spectrum of the object 109 from received measurement data and analyzes the Raman spectrum to perform an identification process of identifying the kind of the object 109 measured. The identification method can be performed by using a feature peak of the Raman spectrum or comparison with known spectrum as disclosed in, for example, Japanese Patent Application Laid-Open No. 2008-209128 and Japanese Patent Application Laid-Open No. H10-038807. In addition to the identification of the kind of the resin material, the computer 121 can conduct analysis such as identification of an additive or an impurity component by performing detection of a specific peak of the Raman spectrum or comparison with a database, which can be typically conducted by Raman spectroscopy. The computer 121 includes a display unit such as a flat panel display and input units such as a keyboard, a mouse, and a touch screen and may receive an instruction from a user or provide information to the user.

In the identification apparatus 1, the optical axis of the illumination optical system 107 and the optical axis of the light capturing optical system 113 intersect each other. More specifically, the optical axis of the illumination optical system 107 and the optical axis of the light capturing optical system 113 intersect each other in a measurement region that is defined on the conveyance surface of the conveyor 108 and through which the object 109 that is conveyed by the conveyor 108 passes. This reduces stray light and enables the Raman-scattered light from the object 109 to be gathered at high sensitivity. The optical axis of the illumination optical system 107 and the optical axis of the light capturing optical system 113 intersect each other and are not coaxial with each other. This enables the illumination optical system 107 and the light capturing optical system 113 to be separately designed and makes it easy to design the optimum structures for the purposes of the systems, which is an advantage.

The illumination optical system 107 is an imaging optical system that has a numerical aperture for the conveyance surface smaller than the numerical aperture of the light capturing optical system 113 for the conveyance surface of the conveyor 108. That is, regarding the illumination optical system 107, the numerical aperture of the condensing lens 106 that condenses the light on the object 109 is smaller than the numerical aperture of the objective lens 110 of the light capturing optical system 113. This enables the depth of focus of the illumination optical system 107 to increase and enables the range of the direction of the optical axis of the illumination optical system 107 to increase with the diameter of the spot of the light that is radiated by the illumination optical system 107 being equal to or smaller than a predetermined value. Consequently, even when the height direction of the object 109 varies, and the distance between the identification apparatus 1 and the object 109 varies, the Raman-scattered light can be stably generated. Consequently, the robustness of the identification apparatus 1 against the variation in the distance between the identification apparatus 1 and the object 109 can be improved.

When the Raman-scattered light having a sufficient intensity for identification can be acquired from the object 109, the condensing lens 106 is not necessarily essential, and the object 109 may be directly irradiated with light that is collimated by the collimator lens 104 and/or the cylindrical lens 105. That is, the illumination optical system 107 may be a collimator optical system that converts the light from the semiconductor laser 101 that serves as the light source into parallel light. In this case, the diameter of the spot of the light that is radiated by the illumination optical system 107 can be substantially the same at any position in the direction of the optical axis of the illumination optical system 107. This enables the robustness against the variation in the distance between the identification apparatus 1 and the object 109 to be improved as described above. The "parallel light" described herein may not be perfect parallel light for diffraction of light and may be substantially parallel light (roughly parallel light).

The numerical aperture (numerical aperture of the objective lens 110) of the light capturing optical system 113 for the conveyance surface is larger than the numerical aperture (numerical aperture of the condensing lens 106) of the illumination optical system 107 for the conveyance surface. This enables the Raman-scattered light to be gathered at an increased solid angle and enables the sensitivity of the identification apparatus 1 to be improved. In other words, an objective numerical aperture (numerical aperture of the objective lens 110) of the light capturing optical system 113 is larger than an objective numerical aperture (numerical aperture of the condensing lens 106) of the illumination optical system 107.

The numerical aperture (numerical aperture of the fiber condensing lens 112) of the light capturing optical system 113 for the optical fiber 114 (for the optical fiber) is preferably smaller than the numerical aperture of the optical fiber 114 that serves as the guide unit. This enables the Raman-scattered light to be guided to the spectroscope 120 with the numerical aperture being substantially larger than the numerical aperture of the optical fiber 114 and enables the sensitivity of the identification apparatus 1 to be improved. When the sensitivity of the identification apparatus 1 is sufficient, the numerical aperture of the objective lens 110 may be equal to or smaller than the numerical aperture of the optical fiber 114, and the fiber condensing lens 112 may be removed.

An angle that is formed between the optical axis of the illumination optical system 107 and the conveyance surface of the conveyor 108 preferably differs from an angle that is formed between the optical axis of the light capturing optical system 113 and the conveyance surface of the conveyor 108. That is, the illumination optical system 107 and the light capturing optical system 113 are preferably asymmetrical with each other with respect to the normal to the conveyance surface of the conveyor 108, which is referred to as non-mirrorlike arrangement.

Figure 2A:
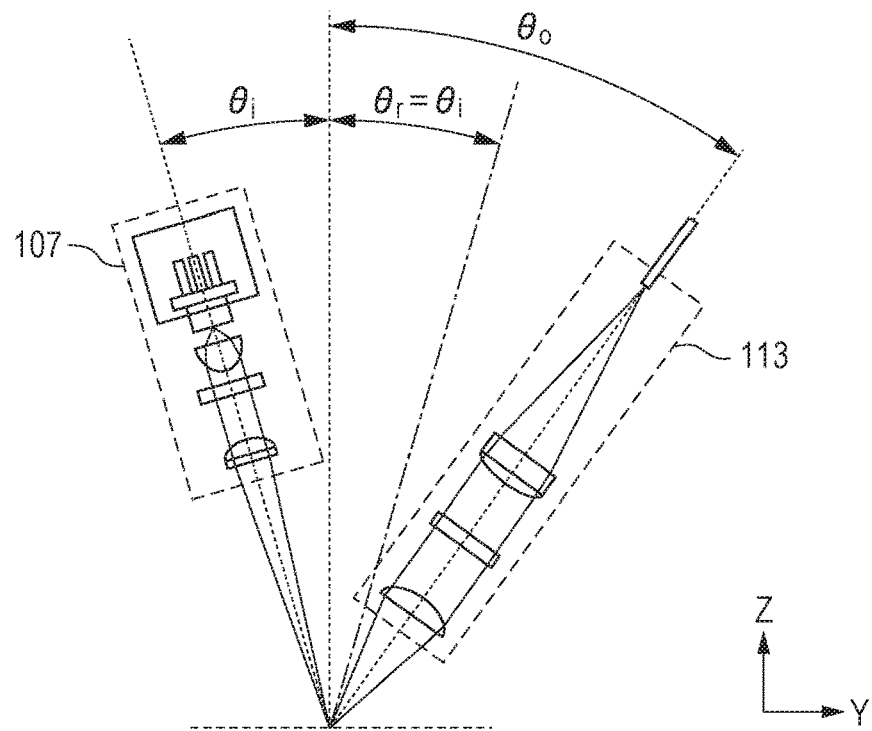
FIG. 2A illustrates an example of optical arrangement of an illumination optical system and a light capturing optical system according to the first embodiment.
Figure 2B:
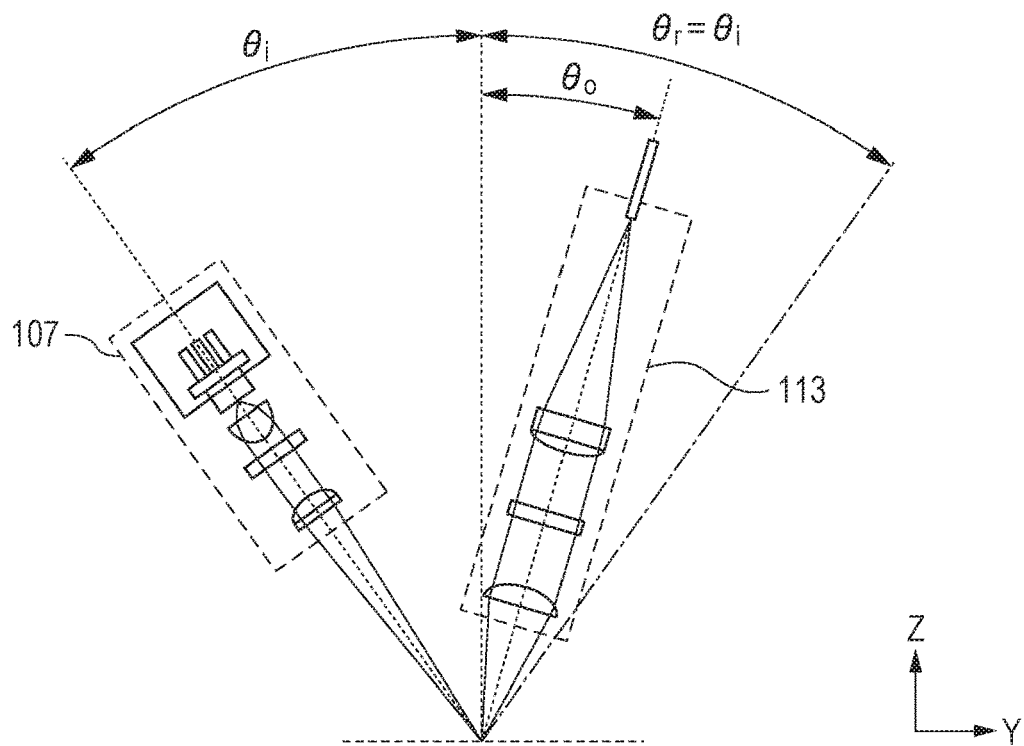
FIG. 2B illustrates an example of the optical arrangement of the illumination optical system and the light capturing optical system according to the first embodiment.

FIG. 2A and FIG. 2B illustrate examples of the optical arrangement of the illumination optical system 107 and the light capturing optical system 113. In FIG. 2A and FIG. 2B, θi (°) is an angle that is formed between the optical axis of the illumination optical system 107 and the normal to the conveyance surface, and θo (°) is an angle that is formed between the optical axis of the light capturing optical system 113 and the normal to the conveyance surface. The angle that is formed between the optical axis of the illumination optical system 107 and the conveyance surface of the conveyor 108 is expressed as (90°−θi). The angle that is formed between the optical axis of the light capturing optical system 113 and the conveyance surface of the conveyor 108 is expressed as (90°−θo). In FIG. 2A and FIG. 2B, one-dot chain lines represent the optical axis of the light capturing optical system 113 with the optical axis of the light capturing optical system 113 and the optical axis of the illumination optical system 107 being in mirrorlike arrangement. The optical axis that is represented by each one-dot chain line means an optical axis along which a reflection light component from the object 109 propagates. θr (°) is an angle that is formed between the optical axis and the normal to the conveyance surface. θr is equal to θi.

In an example of the structure in FIG. 2A, the illumination optical system 107 and the light capturing optical system 113 are arranged such that the angle θo that is formed between the optical axis of the light capturing optical system 113 and the normal to the conveyance surface is larger than θr. Consequently, the light that is radiated by the illumination optical system 107 and that is reflected from the object 109 is not incident on the light capturing optical system 113. When the angle that is formed between the optical axis of the light capturing optical system 113 and the normal to the conveyance surface is larger than the angle in the case of the mirrorlike arrangement, a component of the excitation light that is reflected from the object 109 and that is incident on the spectroscope 120 can be reduced. In the case where the influence of the component of the excitation light that is reflected and that is incident is small, the excitation light cutoff filter 111 may be omitted. The same effect can be achieved in the case where the illumination optical system 107 and the light capturing optical system 113 are arranged such that the angle θo that is formed between the optical axis of the light capturing optical system 113 and the normal to the conveyance surface is smaller than θr as illustrated in FIG. 2B.

Figure 3A:
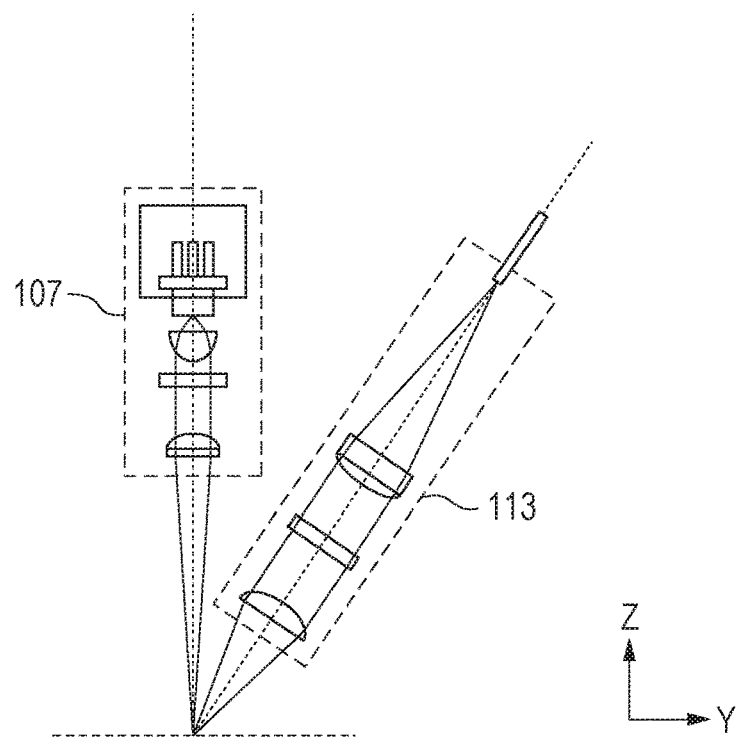
FIG. 3A illustrates another example of the optical arrangement of the illumination optical system and the light capturing optical system according to the first embodiment.
Figure 3B:
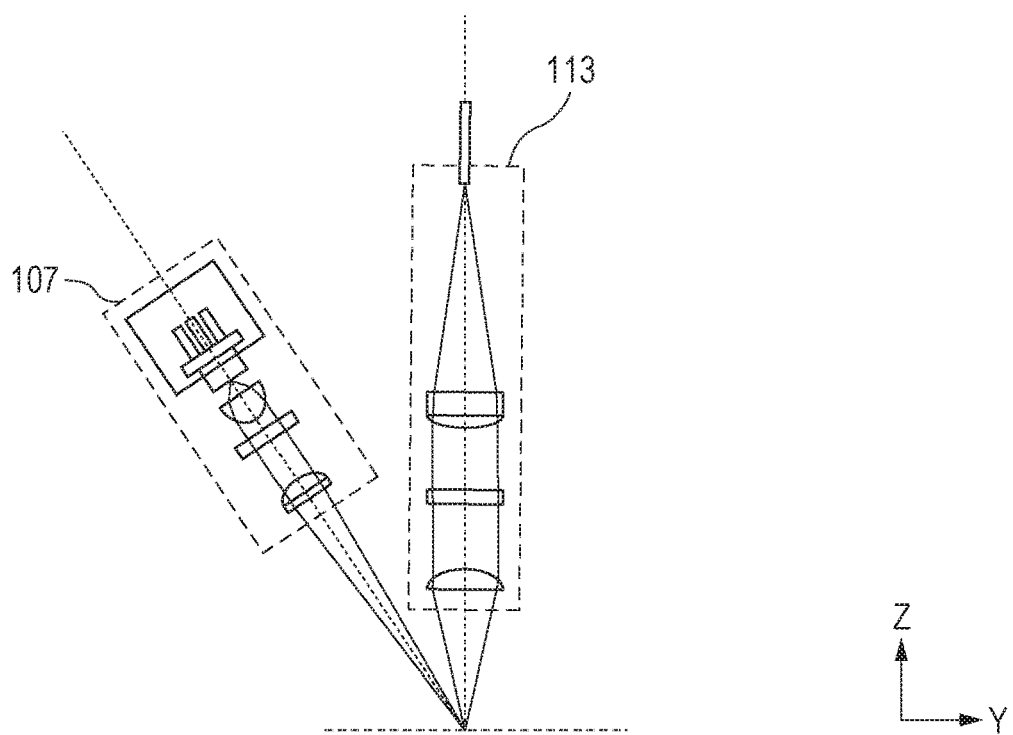
FIG. 3B illustrates another example of the optical arrangement of the illumination optical system and the light capturing optical system according to the first embodiment.

In FIG. 1, FIG. 2A, and FIG. 2B, the illumination optical system 107 and the light capturing optical system 113 are inclined with respect to the normal to the conveyance surface of the conveyor 108 when disposed, but are not limited thereto. As illustrated in FIG. 3A and FIG. 3B, the optical axis of the illumination optical system 107 or the light capturing optical system 113 may extend along the normal to the conveyance surface. That is, the optical axis of the illumination optical system 107 or the light capturing optical system 113 may be perpendicular to the conveyance surface of the conveyor 108.

In the identification apparatus 1 according to the present embodiment, the optical axis of the illumination optical system 107 and the optical axis of the light capturing optical system 113 intersect each other, and the illumination optical system 107 has a numerical aperture smaller than that of the light capturing optical system 113 as described above. Consequently, regarding the identification apparatus that can be provided according to the present embodiment, the stray light is reduced, and the degree of the robustness against the variation in the distance between the identification apparatus 1 and the object 109 that is an object is high.

Second Embodiment

Figure 4:
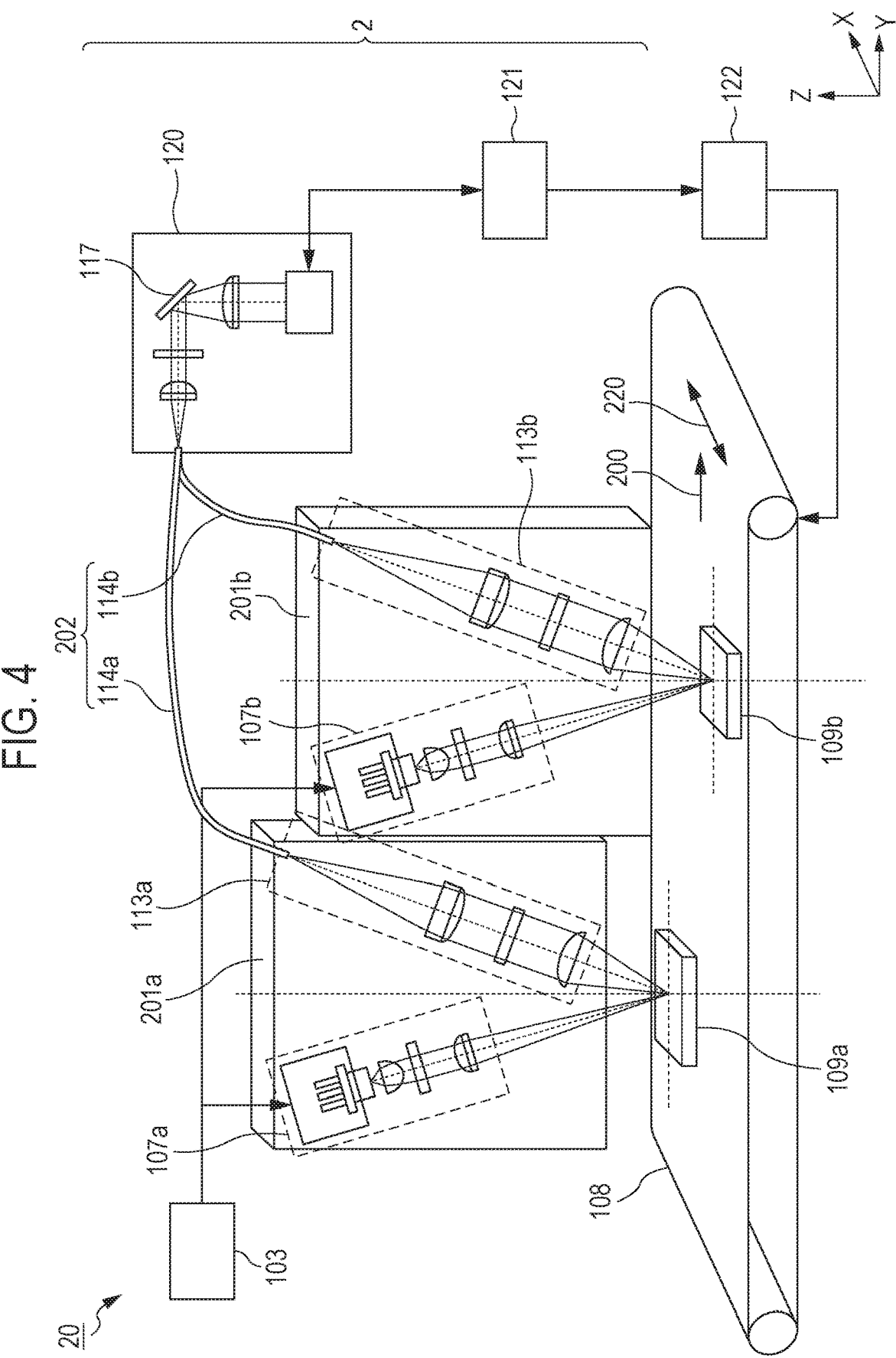
FIG. 4 schematically illustrates the structure of an identification system and an identification apparatus according to a second embodiment.

An identification apparatus according to a second embodiment of the present invention will be described with reference to FIG. 4. Components common to those according to the first embodiment are designated by like reference characters, and a description thereof is omitted in some cases. FIG. 4 schematically illustrates the structure of an identification system and the identification apparatus according to the second embodiment.

An identification apparatus 2 according to the present embodiment includes capturing units 201 each of which includes the illumination optical system 107 and the light capturing optical system 113, and an optical fiber bundle 202 that includes the optical fibers 114 that guide the Raman-scattered light that is captured by the capturing units 201, and the optical fibers 114 are bundled near an exit end of the optical fiber bundle 202. The capturing units 201 face the conveyance surface of the conveyor 108 and are arranged at different positions in the conveyance direction 200 of the conveyor 108 and in the traverse direction of conveyance that is perpendicular to the conveyance direction 200. The identification apparatus 2 identifies the kind of the object 109 that is conveyed by the conveyor 108. An identification system 20 according to a modification to the present embodiment includes the conveyor 108, the conveyor-driving device 122, and the identification apparatus 2 that faces the conveyor 108. FIG. 4 illustrates the identification apparatus 2 that includes two capturing units 201a and 201b. However, the identification apparatus 2 may include three or more capturing units 201.

Each capturing unit 201 includes the illumination optical system 107 and the light capturing optical system 113, illuminates the object 109 that is conveyed by the conveyor 108, and gathers the light from the object 109. The structure of the illumination optical system 107 and the light capturing optical system 113 of the capturing unit 201 is the same as in the first embodiment, and a description thereof is omitted. FIG. 4 illustrates a structure for driving the semiconductor laser 101 of each capturing unit 201 by using the single laser driver 103, which is not a limitation. The laser drivers 103 may be provided for the respective capturing units 201.

The capturing units 201 are arranged at different positions in the traverse direction 220 of conveyance intersecting the conveyance direction 200 of the conveyor 108 as described above. That is, the capturing units 201 are arranged at different positions in the traverse direction 220 of conveyance of the conveyor 108. Each capturing unit 201 irradiates the object 109 with the light in a predetermined region on the conveyance surface of the conveyor 108 and captures Raman-scattered light from the predetermined region. Accordingly, the capturing unit 201 has a limited region for capturing. According to the present embodiment, as illustrated in FIG. 4, the capturing units 201 are provided accordingly, and the capturing units 201 are shifted in the conveyance direction 200 of the conveyor 108 and in the traverse direction 220 of conveyance when disposed. In the case where the capturing units 201 are thus shifted when disposed, a capturing range in which the identification apparatus 2 can identify the kind of the object 109 can be increased. Consequently, the throughput of identification can be improved. In other words, the capturing units 201 are arranged so as to partly overlap when viewed in the traverse direction 220 of conveyance. Such arrangement reduces a non-capturing area in the traverse direction 220 of conveyance, in which capturing is not carried out. In the case where the capturing units 201 are thus shifted in the conveyance direction when disposed, the capturing units 201 do not interfere with each other. In other word, the number of the capturing units 201 that are arranged per unit conveyance width of the conveyor 108, that is, the density of arrangement can be increased. Similarly, in the case where the illumination optical systems 107 are arranged at different positions in the traverse direction 220 of conveyance, the number of times the object is conveyed per unit conveyance width of the conveyor 108 can be increased. In addition, in the case where the illumination optical systems 107 are arranged at different positions in the conveyance direction 200, the illumination optical systems 107 do not interfere with each other, and the density of arrangement of the illumination optical systems 107 per unit conveyance width of the conveyor 108 can be increased. Similarly, in the case where the light capturing optical systems 113 are arranged at different positions in the traverse direction 220 of conveyance, the number of times the object 109 is conveyed per unit conveyance width of the conveyor 108 can be increased. In addition, in the case where the light capturing optical systems 113 are arranged at different positions in the conveyance direction 200, the light capturing optical systems 113 do not interfere with each other, and the density of arrangement of the light capturing optical systems 113 per unit conveyance width of the conveyor 108 can be increased.

The capturing units 201 are preferably arranged at different positions also in the conveyance direction 200 of the conveyor 108. Each capturing unit 201, which includes the illumination optical system 107 and the light capturing optical system 113, has a certain size. Accordingly, in the case where the capturing units 201 are diagonally arranged when viewed in the direction perpendicular to the conveyance surface of the conveyor 108 as described above, the density of the capturing units 201 in the width direction of the conveyor 108 can be increased. Consequently, the identification resolution of the identification apparatus 2 can be increased, and the kind of the resin that is contained in the object 109 having a reduced size can be identified.

The optical fiber bundle 202 serves as a guide unit that guides the Raman-scattered light that is captured by the capturing units 201 to the spectroscope 120. The optical fiber bundle 202 includes the optical fibers 114 that are assigned to the respective capturing units 201. The entrance end of each optical fiber 114 is located such that the light from the light capturing optical system 113 of the assigned capturing unit 201 is incident thereon. The exit end of each optical fiber 114 is bundled such that the Raman-scattered light from the capturing units 201 is guided to the single spectroscope 120. In an example described herein, only the single spectroscope 120 is provided. However, there may be the spectroscopes 120, provided that the number of the spectroscopes 120 is smaller than the number of the capturing units 201. With this structure, the number of the spectroscopes 120, which are typically expensive, can be decreased, and the cost of the identification apparatus can be reduced. In addition, measurement errors and variations due to the spectroscopes 120 can be reduced, and the identification accuracy of the identification apparatus can be improved.

The basic structure of the spectroscope 120 is the same as that according to the first embodiment. However, the present embodiment differs from the first embodiment in that the Raman-scattered light from the capturing units 201 is incident thereon.

In FIG. 4, the optical fibers 114 that are included in the optical fiber bundle 202 are bundled near the exit end (end portion nearer than the other end to the spectroscope 120) of the optical fiber bundle 202 and are arranged in a direction perpendicular to the paper in FIG. 4. In other words, the exit ends of the optical fibers 114 are arranged in a line in the traverse direction 220 of conveyance intersecting the conveyance direction 200. Accordingly, a collection of the Raman-scattered light that is guided by the optical fibers 114 is arranged in the direction perpendicular to the paper and is incident on the spectroscope 120. The collection of the Raman-scattered light is dispersed by the diffraction grating 117 that serves as the spectral element in a direction perpendicular to the direction of arrangement of the optical fibers 114, that is, a direction parallel to the paper in FIG. 4.

According to the present embodiment, an area image sensor is used as the light-receiving element. More specifically, an area image sensor that includes photoelectric conversion elements that are two-dimensionally arranged in the direction perpendicular to the paper in FIG. 4 and in the direction parallel to the paper is used as the light-receiving element. In this case, on a light-receiving surface of the light-receiving element, a spectrum as a result of the single Raman-scattered light being dispersed by the spectral element distributes in the direction parallel to the paper, and the collection of the Raman-scattered light from the optical fibers 114 is arranged in the direction perpendicular to the paper. According to the present embodiment, the use of the area image sensor as the light-receiving element as above enables two or more Raman scattering spectrums on the light-receiving surface to be simultaneously acquired and enables the size and cost of the spectroscope 120 to be reduced.

The computer 121 acquires the spectral data of the Raman-scattered light from the CCD 119 that serves as the light-receiving element as in the first embodiment, analyzes the spectral data, and performs the identification process of identifying the kind of the object 109. In the structure in FIG. 4, the order of the arrangement of the optical fibers 114 that are connected to the spectroscope 120 is the reverse order to that of the collection of the Raman-scattered light that is imaged on the light-receiving surface of the light-receiving element. In view of this, the computer 121 associates the positions of the capturing units 201 with the positions of the spectrums on the light-receiving surface of the light-receiving element or in an acquired image in the identification process. This enables the kind of objects 109a and 109b that are detected by the respective capturing units 201a and 201b to be identified.

The structure of the illumination optical system 107 and the light capturing optical system 113 of each capturing unit 201 and the optical arrangement thereof are the same as those according to the first embodiment. That is, in each capturing unit 201, the optical axis of the illumination optical system 107 and the optical axis of the light capturing optical system 113 intersect each other. The illumination optical system 107 of the capturing unit 201 is the imaging optical system that has a numerical aperture for the conveyance surface smaller than the numerical aperture of the light capturing optical system 113 for the conveyance surface of the conveyor 108, or the collimator optical system that converts the light from the light source into the parallel light. Consequently, even when there are the capturing units 201, the robustness of the identification apparatus 2 against the variation in the distance between the identification apparatus 2 and the object 109 can be improved. In other words, an objective numerical aperture (numerical aperture of the condensing lens 106) of the illumination optical system 107 is smaller than an objective numerical aperture (numerical aperture of the objective lens 110) of the light capturing optical system 113.

Third Embodiment

Figure 5:
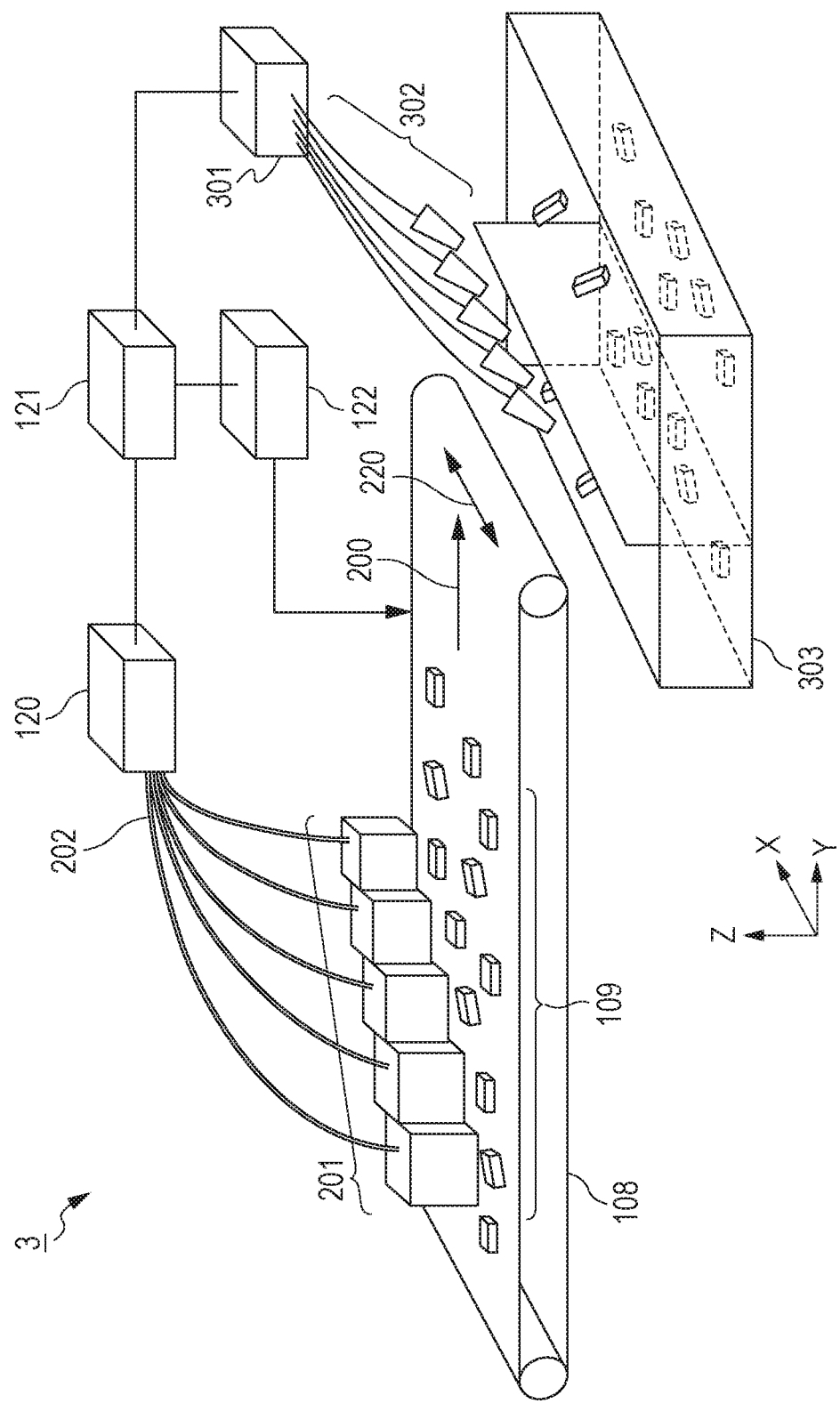
FIG. 5 schematically illustrates the structure of a resin-selecting system according to a third embodiment.

A resin-selecting system according to a third embodiment of the present invention will be described with reference to FIG. 5. Components common to those according to the first embodiment and the second embodiment are designated by like reference characters, and a description thereof is omitted in some cases. FIG. 5 schematically illustrates the structure of the resin-selecting system according to the third embodiment.

A resin-selecting system 3 according to the present embodiment includes the identification apparatus 1 according to the first embodiment or the identification apparatus 2 according to the second embodiment, the conveyor 108, and a selection unit that is disposed nearer than the identification apparatus 1 or 2 to the downstream side of the conveyor 108. The selection unit selects the objects 109, based on an identification result of the identification apparatus 1 or 2. In the following description, the resin-selecting system 3 includes the identification apparatus 2, that is, the capturing units 201 but is not limited thereto. The resin-selecting system 3 may include the single capturing unit 201.

The selection unit of the resin-selecting system 3 according to the present embodiment includes an air-gun-driving device 301 and air guns 302. According to the present embodiment, the selection unit includes the air guns 302 that are arranged in the traverse direction 220 of conveyance intersecting the conveyance direction 200 of the conveyor 108.

The spectroscope 120 transmits, to the computer 121, image data that is acquired by dispersing the light entering through the optical fibers 114 and collecting the spectrums of the Raman-scattered light that is captured by the capturing units 201 as in the second embodiment. The computer 121 extracts Raman spectrums relative to the respective capturing units 201 from the received image data and identifies the kind of the objects 109 that are measurement targets of the capturing units 201.

The computer 121 transmits an air gun driving signal to the air-gun-driving device 301, based on the above identification result. At this time, the computer 121 calculates, for example, conveyance time of the conveyor 108 and air discharge time of the air guns 302 and transmits the air gun driving signal after appropriate delay. Consequently, compressed air can hit only a desired object among the objects 109 while the object falls.

A basket 303 for selection is disposed downstream of the conveyor 108. The objects 109 that are conveyed by the conveyor 108 fly out from an end portion of the conveyor 108, fall, and enter the basket 303 for selection. The basket 303 for selection is divided into small compartments and stores the objects 109 separately for every kind after the selection unit selects.

In an example in FIG. 5, the air guns 302 discharge the compressed air when the air gun driving signal is ON and shoot down only the target object among the objects 109 toward the upstream side in the conveyance direction 200. Consequently, the target object is stored in a small compartment of the basket 303 for selection that is located upstream of the other compartment in the conveyance direction 200.

In this way, the selection unit can select the objects, based on the identification result of the identification apparatus. The above selection unit is an example and is not limited thereto. The selection unit may be another selection unit such as a robot hand.

An arrangement unit that arranges the objects 109 that are conveyed by the conveyor 108 or a preprocessing unit for adjustment such that the shapes or particle sizes of the objects 109 become uniform may be disposed upstream of the conveyor 108. Examples of the arrangement unit and the preprocessing unit include a vibration conveyor, a sifter machine, and a crushing machine that adjusts a particle diameter.

According to the present embodiment, a resin-selecting system that can stably identify and select a large number of objects can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An identification apparatus that identifies a kind of resin that is contained in an object to be conveyed by a conveyor, the identification apparatus comprising:
    an illumination optical system that illuminates the object on a conveyance surface of the conveyor with light from a light source;
    a light capturing optical system that captures Raman-scattered light from the object that is illuminated by the illumination optical system;
    a spectral element that disperses the Raman-scattered light that is captured by the light capturing optical system;
    a light-receiving element that receives the Raman-scattered light that is dispersed by the spectral element; and
    a data-processing unit that acquires spectral data of the Raman-scattered light from the light-receiving element and that performs a process of identifying the object, based on the spectral data,
    wherein an optical axis of the illumination optical system and an optical axis of the light capturing optical system intersect each other, and
    wherein the illumination optical system is an imaging optical system that has a numerical aperture for the conveyance surface smaller than a numerical aperture of the light capturing optical system for the conveyance surface.

2. The identification apparatus according to claim 1, further comprising:
    an optical fiber that guides the Raman-scattered light that is captured by the light capturing optical system to the spectral element.

3. The identification apparatus according to claim 2,
    wherein the numerical aperture of the light capturing optical system for the conveyance surface is larger than a numerical aperture of the light capturing optical system for the optical fiber.

4. The identification apparatus according to claim 3,
    wherein the numerical aperture of the light capturing optical system for the optical fiber is smaller than a numerical aperture of an entrance end of the optical fiber.

5. The identification apparatus according to claim 1,
    wherein an angle that is formed between a conveyance direction of the conveyor and a plane containing the optical axis of the illumination optical system and the optical axis of the light capturing optical system is no less than 0 degrees and no more than 15 degrees.

6. The identification apparatus according to claim 1,
    wherein a plane containing the optical axis of the illumination optical system and the optical axis of the light capturing optical system is parallel to a conveyance direction of the conveyor.

7. The identification apparatus according to claim 1,
    wherein an angle that is formed between the optical axis of the illumination optical system and the conveyance surface differs from an angle that is formed between the optical axis of the light capturing optical system and the conveyance surface.

8. The identification apparatus according to claim 1,
    wherein the light capturing optical system includes a wavelength filter that shields light having at least a wavelength range in the light and allows the Raman-scattered light to pass therethrough, and
    wherein the wavelength filter is disposed on a pupil surface of the light capturing optical system.

9. The identification apparatus according to claim 1,
    wherein the illumination optical system defines an illumination region on the conveyance surface, and
    wherein a width of the illumination region in a conveyance direction of the conveyor is greater than a width of the illumination region in a direction perpendicular to the conveyance direction of the conveyor.

10. The identification apparatus according to claim 1,
    wherein the illumination optical system is a collimator optical system that converts the light from the light source into parallel light.

11. The identification apparatus according to claim 1,
    wherein the light-receiving element is an area image sensor that includes photoelectric conversion elements that are two-dimensionally arranged.

12. The identification apparatus according to claim 1,
    wherein the object is a crushed object.

13. An identification system comprising:
    the identification apparatus according to claim 1; and
    the conveyor.

14. A selection system comprising:
    the identification apparatus according to claim 1;
    the conveyor; and
    a selection unit that is disposed nearer than the identification apparatus to a downstream side of the conveyor and that selects the object, based on an identification result of the identification apparatus.

15. An identification apparatus that identifies a kind of resin that is contained in an object to be conveyed by a conveyor, the identification apparatus comprising:
    capturing units each of which includes an illumination optical system that illuminates the object on a conveyance surface of the conveyor with light from a light source, and a light capturing optical system that captures Raman-scattered light from the object that is illuminated by the illumination optical system, the capturing units facing the conveyance surface of the conveyor and being arranged at different positions in a traverse direction of conveyance intersecting a conveyance direction of the conveyor;
    an optical fiber bundle that includes optical fibers that guide the Raman-scattered light that is captured by the capturing units, the optical fibers being bundled near an exit end of the optical fiber bundle;
    a spectral element that disperses a collection of the Raman-scattered light that is guided by the optical fiber bundle;
    a light-receiving element that receives the collection of the Raman-scattered light that is dispersed by the spectral element; and
    a data-processing unit that acquires spectral data of the collection of the Raman-scattered light from the light-receiving element and that performs an identification process,
    wherein in each of the capturing units, an optical axis of the illumination optical system and an optical axis of the light capturing optical system intersect each other.

16. The identification apparatus according to claim 15,
    wherein in each of the capturing units, the illumination optical system is an imaging optical system that has a numerical aperture for the conveyance surface smaller than a numerical aperture of the light capturing optical system for the conveyance surface.

17. The identification apparatus according to claim 15,
    wherein the illumination optical system is a collimator optical system that converts the light from the light source into parallel light.

18. The identification apparatus according to claim 15, wherein exit ends of the optical fibers are arranged in a line in the traverse direction of conveyance.

19. The identification apparatus according to claim 15, wherein the capturing units are arranged at different positions in the traverse direction of conveyance.

20. The identification apparatus according to claim 15, wherein the capturing units are arranged at different positions in the conveyance direction.

21. The identification apparatus according to claim 15, wherein the capturing units partly overlap when viewed in the traverse direction of conveyance.

22. The identification apparatus according to claim 15, wherein in each of the capturing units, an angle that is formed between the conveyance direction of the conveyor and a plane containing the optical axis of the illumination optical system and the optical axis of the light capturing optical system is no less than 0 degrees and no more than 15 degrees.

23. The identification apparatus according to claim 22, wherein in each of the capturing units, the plane containing the optical axis of the illumination optical system and the optical axis of the light capturing optical system is parallel to the conveyance direction of the conveyor.

24. The identification apparatus according to claim 15, wherein the light-receiving element is an area image sensor that includes photoelectric conversion elements that are two-dimensionally arranged.

25. The identification apparatus according to claim 15, wherein the object is a crushed object.

26. An identification system comprising:
the identification apparatus according to claim 15; and the conveyor.

27. A selection system comprising:
the identification apparatus according to claim 15;
the conveyor; and
a selection unit that is disposed nearer than the identification apparatus to a downstream side of the conveyor and that selects the object, based on an identification result of the identification apparatus.

28. An identification apparatus that identifies a kind of resin that is contained in an object to be conveyed by a conveyor, the identification apparatus comprising:
an illumination optical system that illuminates the object on a conveyance surface of the conveyor with light from a light source;
a light capturing optical system that captures Raman-scattered light from the object that is illuminated by the illumination optical system;
a spectral element that disperses the Raman-scattered light that is captured by the light capturing optical system;
a light-receiving element that receives the Raman-scattered light that is dispersed by the spectral element; and
a data-processing unit that acquires spectral data of the Raman-scattered light from the light-receiving element and that performs a process of identifying the object, based on the spectral data,
wherein an optical axis of the illumination optical system and an optical axis of the light capturing optical system intersect each other, and
wherein the illumination optical system is an imaging optical system that has an objective numerical aperture smaller than an objective numerical aperture of the light capturing optical system.

* * * * *